(12) United States Patent
Krug

(10) Patent No.: US 7,887,237 B2
(45) Date of Patent: Feb. 15, 2011

(54) COOLING SYSTEM FOR GANTRY-MOUNTED COMPONENTS OF A COMPUTED TOMOGRAPHY SYSTEM

(75) Inventor: Rita Krug, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/188,332

(22) Filed: Aug. 8, 2008

(65) Prior Publication Data

US 2009/0041181 A1 Feb. 12, 2009

(30) Foreign Application Priority Data

Aug. 8, 2007 (DE) ........................ 10 2007 037 313

(51) Int. Cl.
*H05G 1/02* (2006.01)
*H05G 1/00* (2006.01)
(52) U.S. Cl. ........................................ 378/199; 378/204
(58) Field of Classification Search ............... 378/4–20, 378/199, 204, 210
See application file for complete search history.

(56) References Cited

U.S. PATENT DOCUMENTS

| 4,866,743 | A | * | 9/1989 | Kroener | 378/4 |
| 4,953,655 | A | * | 9/1990 | Furukawa | 181/160 |
| 4,969,167 | A | | 11/1990 | Zupancic et al. | |
| 6,909,775 | B2 | * | 6/2005 | Ray et al. | 378/141 |
| 6,988,827 | B2 | | 1/2006 | Mueller | |
| 7,102,308 | B2 | * | 9/2006 | Lacey et al. | 318/268 |
| 7,338,208 | B2 | * | 3/2008 | Lacey | 378/199 |
| 7,488,949 | B2 | * | 2/2009 | Ueno et al. | 250/370.15 |
| 2004/0202287 | A1 | * | 10/2004 | Muller | 378/199 |
| 2004/0228450 | A1 | * | 11/2004 | Mueller | 378/199 |
| 2006/0215808 | A1 | * | 9/2006 | Lacey | 378/19 |
| 2007/0274437 | A1 | | 11/2007 | Schindler et al. | |
| 2007/0284535 | A1 | * | 12/2007 | Heismann et al. | 250/370.15 |

\* cited by examiner

*Primary Examiner*—Edward J Glick
*Assistant Examiner*—Anastasia Midkiff
(74) *Attorney, Agent, or Firm*—Schiff Hardin LLP

(57) ABSTRACT

A computed tomography apparatus has a gantry for mounting components of an acquisition system that are arranged such that they can rotate around a system axis, and a stationary part in which the gantry is supported such that it can tilt. A device for cooling the components by airflow is arranged on the gantry. The cooling device has at least one feed channel and at least one air discharge channel that are arranged between the stationary part and the gantry so that the air current introduced into the gantry via the stationary part is conducted out from the gantry into the stationary part in a directed manner after cooling the components. The direction of the air current directed from the computed tomography apparatus thus does not depend on the tilt of the gantry. Moreover, the computed tomography apparatus is designed such that cooling is achieved with low noise emission since the direct sound propagation path between the exit opening and the gantry is interrupted.

20 Claims, 2 Drawing Sheets

COOLING SYSTEM FOR GANTRY-MOUNTED COMPONENTS OF A COMPUTED TOMOGRAPHY SYSTEM

BACKGROUND OF THE INVENTION

1. Field of the Invention

The present invention concerns a computed tomography apparatus of the type having a gantry at which components of an acquisition system are mounted such that the gantry and the components rotate around a system axis, a stationary part in which the gantry is supported such that it can tilt, and a cooling device for cooling the components mounted at a gantry by means of an air flow.

2. Description of the Prior Art

Three-dimensional slices images of an examination region of a patient are generated with computed tomography apparatuses for diagnosis or therapy the use of x-rays. At typical computed tomography apparatus has a gantry for mounting components of an acquisition system arranged such that they can rotate around a system axis, and a stationary part in which the gantry is supported. To acquire projections of an examination region of a subject, the acquisition system has, as one of the components a component a radiator in the form of an x-ray tube and, as another of the components, a detector arranged opposite the x-ray tube. Projections from a number of different projection directions at various positions along the examination region are acquired by a rotation of the gantry simultaneously with a continuous feed in the direction of the system axis of a patient on a mobile platform on a support device. The projections acquired in this manner with a helical scan are transmitted to a computer and a three-dimensional slice image is calculated (computed) therefrom which, for example, can be presented on a display unit.

A fundamental heat problem is present in all computed tomography apparatuses because 99% of the electrical energy used in the generation by x-ray radiation of the x-ray tube is converted into heat energy. To ensure proper operation of the computed tomography apparatus, it is necessary to dissipate the heat from the gantry in order to avoid overheating the x-ray tube. This is particularly the case when high x-ray power is required for scanning the examination region. Not only the x-ray tube, but also the detector, must be cooled during the operation of the computed tomography apparatus, because otherwise the signal-to-noise ratio of the acquired measurement values degrades with increasing temperature of the detector, which designates the image quality of the reconstructed slice images.

Cooling of the components arranged on the gantry can be achieved with high expenditure because the gantry normally rotates continuously around the examination region during the entire radiological examination. The dissipation of the heat during operation of the computed tomography apparatus proves to be complicated and problematic due to this continuously present rotation movement.

A computed tomography apparatus that has a cooling device for cooling the components of the acquisition system arranged on the gantry by means of an air flow is known from U.S. Pat. No. 4,969,167. The stationary part and the gantry of the known computed tomography apparatus are enclosed by a common housing. A removable housing wall, which is arranged parallel to the acquisition plane and serves to cover the internal components of the computed tomography apparatus thereby, has an air feed channel. The air feed channel is arranged in the immediate proximity of the rotating acquisition system and extends in a circle along the periphery of the gantry. To cool the x-ray tube and the detector, the air feed channel contains along its periphery a number of outlet openings via which an air flow for cooling is dispensed onto the rotating components of the gantry. This air flow is produced by a generator that is associated with the stationary part of the gantry and is connected to the air feed channel. The cooling is achieved by the openings in the air feed channel being arranged close to one another and having only a slight separation from the rotating gantry.

Computed tomography apparatuses of the more recent generation have a gantry that is supported such that it can be tilted relative to the stationary part of the computed tomography apparatus. The gantry and the stationary part thus have separate housings. In contrast to the computed tomography apparatus described above, the components of the acquisition system are cooled by an air flow fed into the housing of the gantry, with outlet openings being provided above the housing from which the air flow can be exhausted (discharged). The air flow is thus dissipated into the examination room in different directions depending on the tilt of the gantry relative to the stationary part of the computed tomography apparatus.

SUMMARY OF THE INVENTION

An object of the present invention is to provide a computed tomography apparatus with a gantry that is supported such that it can be tilted relative to a stationary part, wherein cooling of the components of the acquisition system arranged on the gantry is implemented in an improved form.

The invention is based on the recognition that, in specific situations, a person standing in front of a computed tomography apparatus is exposed to a bothersome continuous draft due to the change in direction of the exhausted, heated air flow that occurs with the tilting of the gantry. This air flow can lead to hygienic problems in the case of surgical interventions in the area of open wounds or incisions. The invention is also based on the recognition that discharge heated air from openings of the housing of the gantry is associated with a high noise emission since the outlet openings are located in the immediate proximity of the rotating components of the acquisition system. For example, noise from the anode rotation of the x-ray tube and noise of the rotational bearing can travel outward essentially without any hindrance.

According to the invention a computed tomography apparatus has a gantry for mounting components of an acquisition system that are arranged such that they can rotate around a system axis, a stationary part in which the gantry is supported such that it can be tilted, and a cooling device for cooling the components arranged on the gantry by means of an air flow, the cooling device having at least one air feed channel and at least one air discharge channel that are arranged between the stationary part and the gantry so that the air flow introduced into the gantry via the stationary part is conducted out from the gantry in a directed (confined or constrained) manner after cooling the components and back into the stationary part.

Because the heated air is discharged in a directed manner into the stationary part, the direction of the air flow thereby arising is independent of a tilt of the gantry and can be rerouted so that an operator is not disrupted. In this way it can also be ensured that the air flow does not lead to a hygienic problem in interventions given tilting of the gantry.

By omitting outlet openings in the gantry housing, noise emission due to rotating components of the gantry is reduced since the direct sound propagation path between noise-causing components and outlet openings is interrupted.

In an embodiment, the cooling device has an air directing channel connected to the air discharge channel. Via the air directing channel a deflection of the air flow exiting from the air discharge channel is produced, this deflection occurring at a predetermined angle. The direct sound path is even more significantly interrupted due to the deflection of the air flow, and this leads to a further sound reduction. The causes of such a sound reduction are, for example, lossy reflections of sound waves on the inner wall of the air feed channel. A particularly effective sound reduction occurs at deflection angles>90°.

For further noise reduction, the air direction channel can be clad with a sound-damping material, or can be formed of a sound-damping material. The sound reduction achieved overall can be increased in this manner with simple measures since the production of such an air direction channel is possible with little effort.

The sound-damping material advantageously has a stronger sound damping in a frequency range in which noise is generated by at least one of the components than in the remaining frequency ranges. The components of the acquisition system arranged on the gantry respectively generate a noise emission characteristic of the components in a frequency range that is for the most part very small. For example, due to the high rotation speed of the anode the x-ray tube generates a high noise level at very high frequencies within a very narrow frequency band. In this way, the noise emissions of individual components can be suppressed very selectively in an effective manner by the proposed damping material.

The sound-damping material advantageously is a mineral fiber. This material possesses a good absorption property in a broad frequency band, such that noises over a broad frequency band are uniformly absorbed in addition to a selective fading of individual frequency ranges.

The gantry is advantageously mounted or supported so it can be tilted by means of two oppositely arranged bearings, and in an embodiment the air feed channel is integrated into a first of those bearings and the air discharge channel is integrated into the oppositely arranged second bearing. In this manner no additional measures are necessary to realize the channels.

In an embodiment of the invention, the air feed channel and/or the air discharge channel is formed by a tube made from a flexible material. The flexibility of the material allows the channels to enable a non-disruptive safe infeed and discharge of the air flow even given tilting of the gantry.

In a further embodiment, the cooling device has a coupling element with which the air discharge channel can be coupled to a climate control system of an examination room. The cooling of the components arranged on the gantry thus does not lead to a heating of the examination room. Also, no disruptive draft is thus generated in the examination room by the escaping, heated air.

The cooling device can be a compressor for generation of an air flow by means of compressed air. The use of compressed air allows the thermodynamic property to be utilized for cooling the components that the temperature automatically decreases due to expansion of the compressed air.

DESCRIPTION OF THE PREFERRED EMBODIMENTS

Figure 1:
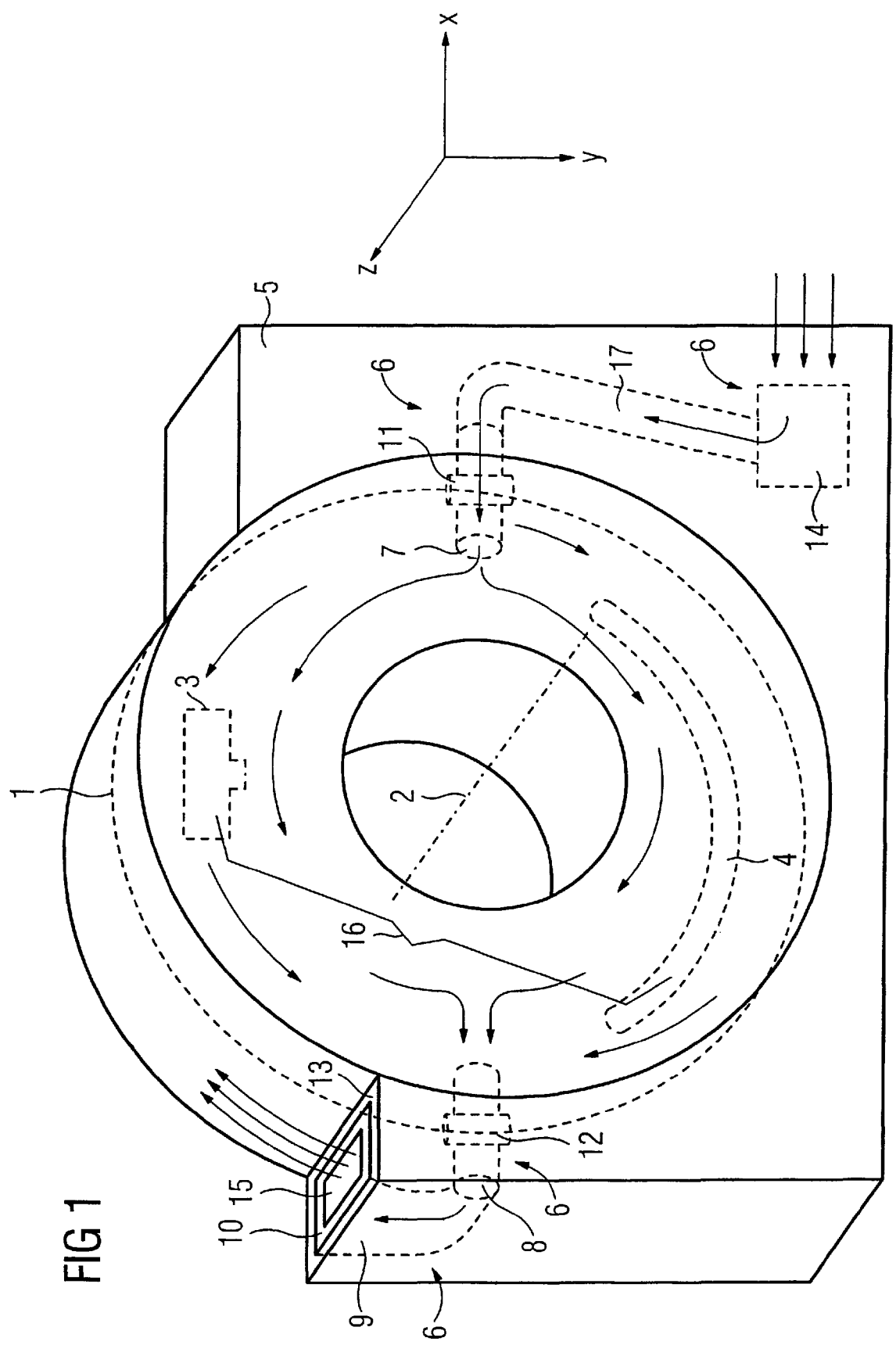
FIG. 1 is a perspective view of an embodiment of a computed tomography apparatus according to the invention wherein the essential components inside the housing of the computed tomography apparatus are shown with dashed lines.

Located inside the computed tomography apparatus according to the invention that is shown in a perspective view in FIG. 1 is an acquisition system 16, arranged such that it can rotate around a system axis 2 on a gantry 1, for acquisition of projections of an examination region from a number of different projection directions. The acquisition system 16 is essentially formed by two components namely an x-ray tube 3 and a detector 4.

A patient support device (not shown) with a movable table plate on which a patient can be borne is associated with the computed tomography apparatus. The table plate can be displaced in the direction of the system axis 2 so that an examination region of the patient can be moved through the opening in the housing of the gantry 1 into the measurement region of the acquisition system 16. The patient and the acquisition system 16 can be displaced relative to one another in this manner in the direction of the system axis 2 so that different scanning functions can be implemented.

The detector 4 is fashioned as an arc arranged opposite the x-ray tube 3. It is formed of multiple detector elements arranged in detector rows. The x-ray tube 3 generates a beam in the form of a fan-shaped x-ray beam that passes through the measurement region of the acquisition system 16. The x-ray radiation subsequently strikes the detector elements of the detector 4. The detector elements generate an attenuation value dependent on the attenuation of the x-ray radiation passing through the measurement region of the acquisition system 16. The conversion of x-ray radiation into an attenuation value respectively ensues by means of a photodiode optically coupled with a scintillator or by means of a directly converting semiconductor, for example. The detector 4 generates a set of attenuation values that are acquired for a specific projection direction of the acquisition system 16.

Projections from a number of different projection directions are acquired at different positions along the examination region via rotation of the gantry 1 given simultaneous, continuous feed of the patient in the direction of the system axis 2. The projections acquired in this manner in a helical scan are transmitted to a computer (not shown) and computed into a three-dimensional slice image which can be shown on a display unit.

The gantry 1 is mounted and supported in a stationary part 5 of the computed tomography apparatus by means of two coaxial bearings 11, 12 on opposite sides such that the gantry 1 can tilt. Such a design in particular has the advantage that an alteration of the orientation of the image plane can be made relative to the patient by tilting the gantry 1 so that, for example, slice images can be generated parallel to the surfaces of an organ, or along vessels.

The computed tomography apparatus has a cooling device 6 to cool the components 3, 4 arranged on the gantry 1, for example the components of the acquisition system 16 (including the x-ray tube 3 and the detector 4). The air for cooling is drawn from the environment by a compressor 14 associated with the stationary part 5 and is supplied via a tube 17 to the air feed channel 7. In the shown example the air feed channel is an integral component of the first coaxial bearing 11 via which the gantry 1 is borne so that it can pivot on the stationary part 5. For example, the axle of the bearing 11 can be fashioned as a tube through which the airflow to be cooled is directed. The compressed air is fed into the region of the gantry 1 via the air feed channel 7 and thereby flows around the components 3, 4 of the gantry 1 that are to be cooled. The thermodynamic effect is thereby utilized for cooling, namely that a decrease in temperature occurs with the expansion of the compressed air. The heated air can escape from the gantry 1 into the stationary part 5 at the opposite side of the air feed channel 7 by means of the air discharge channel 8. In the shown exemplary embodiment, the air discharge channel 8 is an integral component of the second coaxial bearing 12, wherein the channel is formed by a tube-shaped embodiment of the axial bearing 12. It is also possible to form the air feed channel 7 and the air discharge channel 8 separate from the bearings 11, 12. For example, it would be possible for the channels to be formed by flexible hoses.

An air direction channel 9 via which a deflection of the escaping air flow by a predetermined angle (in this case an angle greater than 90°) is produced is connected to the air discharge channel 8. The direct sound path is interrupted by the deflection of the air, and an additional sound insulation occurs due to lossy reflections of the sound waves.

Figure 2:
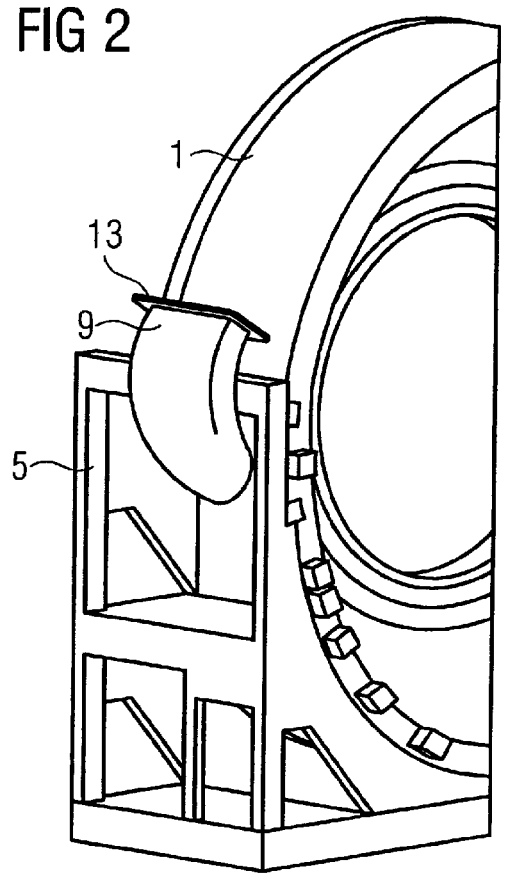
FIG. 2 is a perspective view of a portion of the computed tomography apparatus according to the invention without a housing, with an air directing channel connected to the air discharge channel.

FIG. 2 shows in perspective view of a portion of the computed tomography apparatus without a housing so that the air direction channel 9 is visible. The air direction channel 9 is mounted in the stationary part 5 of the computed tomography apparatus and is directly connected to the air discharge channel 8 in the region of the second bearing 12 shown in FIG. 1. A deflection of the air by more than 90° is produced by the arc-shaped embodiment of the air feed channel 9.

Figure 3:
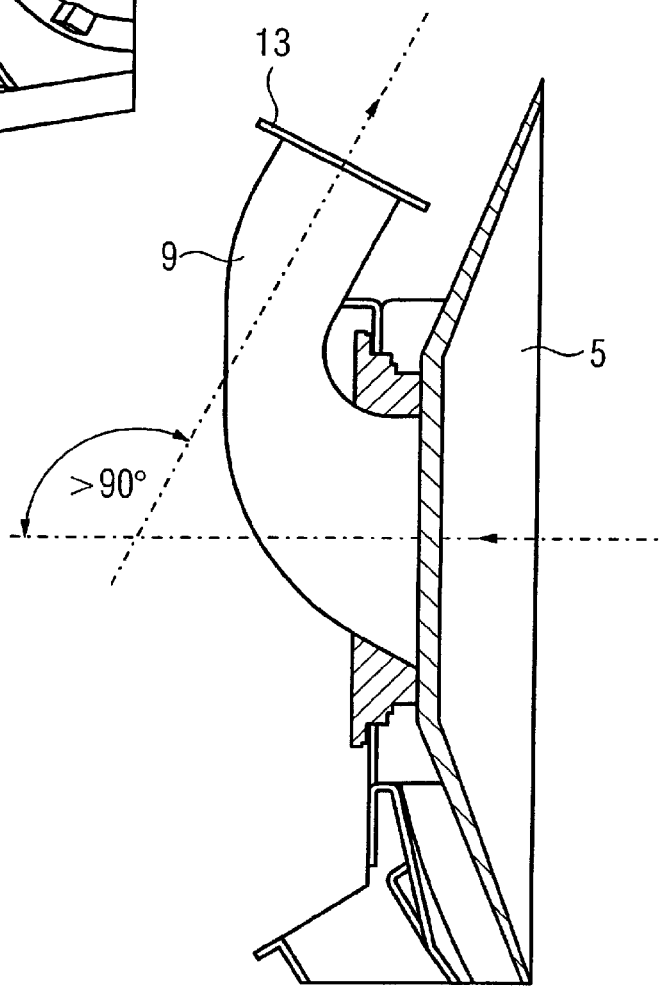
FIG. 3 is a cross-section of the computed tomography apparatus shown in FIG. 2, in a section in the exposure (image acquisition) plane in the region of the air discharge channel.

FIG. 3 shows a cross-section of a section of the computed tomography apparatus of FIG. 1 in the region of the air discharge channel 8. The section is in the exposure plane of the acquisition system 16. From FIG. 3 can be seen that the design of the air direction channel 9 is selected such that the blown air flow is deflected by an angle greater than 90°, so the direct sound path between noise-generating components of the gantry and the exit opening 15 is interrupted.

As an additional measure for noise reduction, the air direction channel 9 has an inner cladding that is produced from a sound-damping material 10. A mineral fiber with which an absorption of sound waves in a broad frequency band ensues uniformly is generally suitable as a sound-damping material 10. For example, rock wool or glass wool are suitable as mineral fibers.

Moreover, the sound-damping material 10 can be designed so that a stronger sound damping exists in a specific frequency range in which one of the components generates noise, than in the remaining frequency ranges. The selective damping in individual frequency ranges. The selective damping in individual frequency ranges is possible, for example, by forming the sound-damping material 10 of different layers that respectively exhibit different acoustic impedances relative to one another. For example, this could be achieved by slices being arranged at a specific distance from one another, with a gas with a specific acoustic impedance or air being introduced into the interstices. It would also be possible for the air direction channel 9 itself to be produced from a sound-damping material 10.

The cooling device 6 has a coupling element 13 with which the air direction channel 9 can be coupled to a climate control system of the examination room. The coupling element 13 is arranged at the end of the air direction channel 9 and is designed such that a coupling to the climate control system can be achieved via a hose by means of a plug or clamp connection.

The measures described above for an embodiment of the computed tomography apparatus, avoid the cooling device 6 directing an air flow into the examination room that is dependent on the tilt of the gantry relative to the stationary part of the computed tomography apparatus, while at the same time a significant reduction of the sound emission occurs because the direct sound path between the rotating gantry and the outlet opening is interrupted.

In summary, the invention concerns a computed tomography apparatus with a gantry 1 for mounting components 3, 4 of an acquisition system 16 that are arranged such that they can rotate around a system axis 2, with a stationary part 5 in which the gantry 1 is borne such that it can tilt, and with a cooling device 6 for cooling the components 3, 4 arranged on the gantry by means of an air flow. The cooling device 6 has at least one feed channel 7 and at least one air discharge channel 8 that are arranged between the stationary part 5 and the gantry 1 so that the air current introduced into the gantry 1 via the stationary part 5 is conducted out from the gantry 1 into the stationary part 5 in a directed manner after cooling the components 3, 4. The direction of the air current directed from the computed tomography apparatus thus does not depend on the tilt of the gantry 1. Moreover, the computed tomography apparatus according to the invention is designed such that cooling is possible with low noise emission since the direct sound path between the exit opening 15 and the gantry 1 is interrupted.

Although modifications and changes may be suggested by those skilled in the art, it is the intention of the inventor to embody within the patent warranted hereon all changes and modifications as reasonably and properly come within the scope of her contribution to the art.

I claim as my invention:

1. A computed tomography apparatus comprising:

a stationary apparatus part;

a gantry mounted at said stationary part for rotation around a system axis, said gantry being mounted at said stationary part so as to be tiltable around a tilting axis extending perpendicularly relative to said system axis;

a plurality of apparatus components carried by said gantry for co-rotation with said gantry around said system axis, said plurality of components including computed tomography data acquisition components configured to acquire computed tomography data as said gantry rotates around said system axis;

a cooling device that cools at least said computed tomography data acquisition components, said cooling device including an airflow channel in said gantry having at least one air feed channel and at least one air discharge channel located between said stationary part and said gantry to introduce an airflow into the gantry from the stationary part, with said airflow being conducted out of said gantry via said at least one air discharge channel, said at least one air discharge channel being oriented and configured to produce a directed discharge of said airflow in a predetermined discharge direction; and said cooling device comprising an air directing channel connected to said air discharge channel configured to deflect the airflow exiting from the air discharge channel at a predetermined angle relative to said tilting axis, and said air directing channel comprising channel walls covered with a cladding, said cladding being comprised of a sound-damping material.

2. A computed tomography apparatus as claimed in claim 1 wherein said angle is greater than 90°.

3. A computed tomography apparatus as claimed in claim 1 wherein said sound-damping material damps sounds more strongly in a frequency range in which noise is generated by at least one of said apparatus components, than in remaining frequency ranges.

4. A computed tomography apparatus as claimed in claim 1 wherein said sound-damping material is a mineral fiber.

5. A computed tomography apparatus as claimed in claim 1 comprising two oppositely mounted bearings at said stationary part that supports said gantry for tilting around said tilting axis, and wherein said at least one air feed channel is integrated into a first of said bearings and said at least one air discharge channel is integrated into a second of said bearings.

6. A computed tomography apparatus as claimed in claim 1 wherein said at least one air feed channel is formed by a tube comprised of flexible material.

7. A computed tomography apparatus as claimed in claim 1 wherein said at least one air discharge channel is formed by a tube comprised of a flexible material.

8. A computed tomography apparatus as claimed in claim 1 wherein each of said at least one air feed channel and said at least one air discharge channel is formed by a tube consisting of a flexible material.

9. A computed tomography apparatus as claimed in claim 1 wherein said cooling device comprises a coupling element configured to couple the airflow discharged from said at least one air discharge channel into a climate control system of an examination room in which said stationary part is located.

10. A computed tomography apparatus as claimed in claim 1 wherein said cooling device comprises a compressor that generates said airflow as a flow of compressed air.

11. A computed tomography apparatus as claimed in claim 1 wherein said angle is greater than 90°.

12. A computed tomography apparatus comprising:
a stationary apparatus part;
a gantry mounted at said stationary part for rotation around a system axis, said gantry being mounted at said stationary part so as to be tiltable around a tilting axis extending perpendicularly relative to said system axis;
a plurality of apparatus components carried by said gantry for co-rotation with said gantry around said system axis, said plurality of components including computed tomography data acquisition components configured to acquire computed tomography data as said gantry rotates around said system axis;
a cooling device that cools at least said computed tomography data acquisition components, said cooling device including an airflow channel in said gantry having at least one air feed channel and at least one air discharge channel located between said stationary part and said gantry to introduce an airflow into the gantry from the stationary part, with said airflow being conducted out of said gantry via said at least one air discharge channel, said at least one air discharge channel being oriented and configured to produce a directed discharge of said airflow in a predetermined discharge direction; and
said cooling device comprising an air directing channel connected to said air discharge channel configured to deflect the airflow exiting from the air discharge channel at a predetermined angle relative to said tilting axis, and said air directing channel comprising channel walls formed of a sound-damping material.

13. A computed tomography apparatus as claimed in claim 12 wherein said sound-damping material damps sounds more strongly in a frequency range in which noise is generated by at least one of said apparatus components, than in remaining frequency ranges.

14. A computed tomography apparatus as claimed in claim 12 wherein said sound-damping material is a mineral fiber.

15. A computed tomography apparatus as claimed in claim 12 comprising two oppositely mounted bearings at said stationary part that supports said gantry for tilting around said tilting axis, and wherein said at least one air feed channel is integrated into a first of said bearings and said at least one air discharge channel is integrated into a second of said bearings.

16. A computed tomography apparatus as claimed in claim 12 wherein said at least one air feed channel is formed by a tube comprised of flexible material.

17. A computed tomography apparatus as claimed in claim 12 wherein said at least one air discharge channel is formed by a tube comprised of a flexible material.

18. A computed tomography apparatus as claimed in claim 12 wherein each of said at least one air feed channel and said at least one air discharge channel is formed by a tube consisting of a flexible material.

19. A computed tomography apparatus as claimed in claim 12 wherein said cooling device comprises a coupling element configured to couple the airflow discharged from said at least one air discharge channel into a climate control system of an examination room in which said stationary part is located.

20. A computed tomography apparatus as claimed in claim 12 wherein said cooling device comprises a compressor that generates said airflow as a flow of compressed air.

* * * * *